United States Patent [19]
Inoue et al.

[11] Patent Number: 5,886,347
[45] Date of Patent: *Mar. 23, 1999

[54] ANALYTICAL METHOD FOR MULTI-COMPONENT AQUEOUS SOLUTIONS AND APPARATUS FOR THE SAME

[75] Inventors: Masaru Inoue; Juichiro Ukon; Issei Yokoyama; Takashi Hagiwara, all of Miyanohigashi-machi, Japan

[73] Assignee: Horiba, Ltd., Kyoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 503,314
[22] Filed: Jul. 13, 1995

[30] Foreign Application Priority Data

Jul. 13, 1994 [JP] Japan ..................................... 6-185409

[51] Int. Cl.$^6$ ........................... G01N 21/25; G01N 21/35
[52] U.S. Cl. ................................. 250/339.12; 250/339.04; 250/341.5
[58] Field of Search ........................ 250/339.12, 339.01, 250/339.04, 339.07, 339.09, 341.5, 343, 346

[56] References Cited

U.S. PATENT DOCUMENTS

| | | |
|---|---|---|
| 4,660,151 | 4/1987 | Chipman et al. . |
| 5,131,740 | 7/1992 | O'Rouke et al. ........................ 356/325 |
| 5,223,715 | 6/1993 | Taylor ....................................... 250/343 |
| 5,242,602 | 9/1993 | Richardson et al. ..................... 210/748 |
| 5,361,628 | 11/1994 | Marko et al. .............................. 73/116 |
| 5,494,032 | 2/1996 | Robinson et al. ......................... 356/41 |
| 5,605,838 | 2/1997 | Backhaus et al. ........................ 436/34 |

Primary Examiner—Edward P. Westin
Assistant Examiner—Richard Hanig
Attorney, Agent, or Firm—Oppenheimer Wolff & Donnelly LLP

[57] ABSTRACT

An analytical method capable of easily, rapidly, and accurately determining concentrations of a multi-component aqueous solution. Near-infrared spectra of a standard solution containing k components of known concentrations are measured n times within a range of 1,500 to 1,850 nm. A loading matrix of p columns by m rows and an intermediate matrix of k columns by m rows for an appointed factor number m are obtained from a response matrix of p columns by n rows consisting of p absorbance values of the respective spectra in a calibration stage and p absorbance values of a near-infrared spectrum within a wavelength range of 1,500 to 1,850 nm of a test liquid. The test liquid contains k components including pure water of unknown concentrations. The concentrations of the k components are determined from a group of absorbance values and the loading and intermediate matrices obtained in the calibration stage by a matrix operation in an prediction stage. In the calibration stage, k+1 characteristic contents can be obtained by adding a solution temperature as one of characteristic items, and k concentration values and one temperature value can be obtained in the prediction stage.

15 Claims, 9 Drawing Sheets

ANALYTICAL METHOD FOR MULTI-COMPONENT AQUEOUS SOLUTIONS AND APPARATUS FOR THE SAME

BACKGROUND OF THE INVENTION

1. Field of the Invention

The present invention relates to an analytical method for multi-component aqueous solutions and an apparatus for the same, and, in particular, to a method for determining concentration values of a plurality of components from a near-infrared absorption spectrum and an apparatus for the same, which method and apparatus are used in fields such as semiconductor processing and food processing.

2. Description of the Prior Art

Figure 12A:
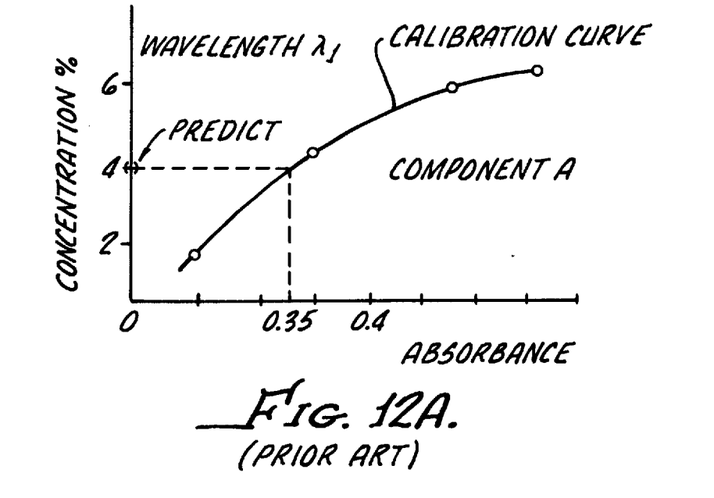
FIGS. 12(A) and 12(B) are graphs of calibration curves used in conventional analytical methods.
Figure 12B:
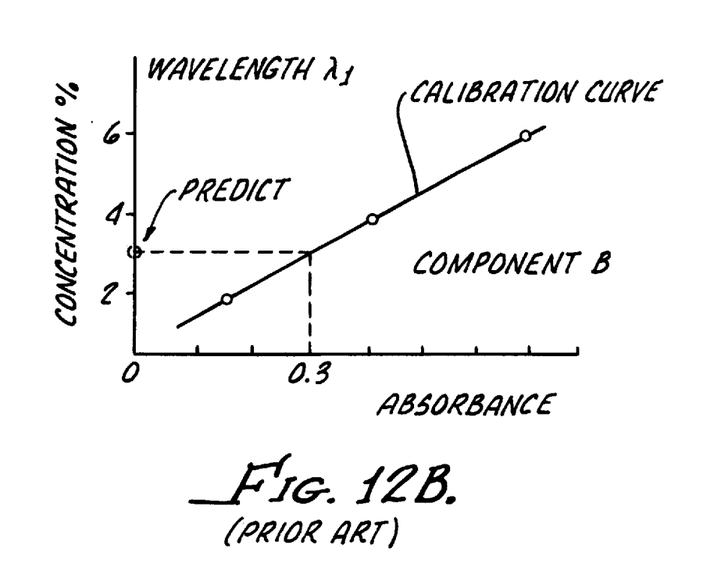

In an analytical system for determining concentrations of a multi-component aqueous solution by the use of a spectrophotometer, absorbance (optical absorptivities) has been measured at absorptive wavelengths inherent to the respective components, and their values have been compared with known calibration curves previously obtained for standard samples, as shown in, for example, FIGS. 12(A) and (B), to determine concentrations.

Figure 13:
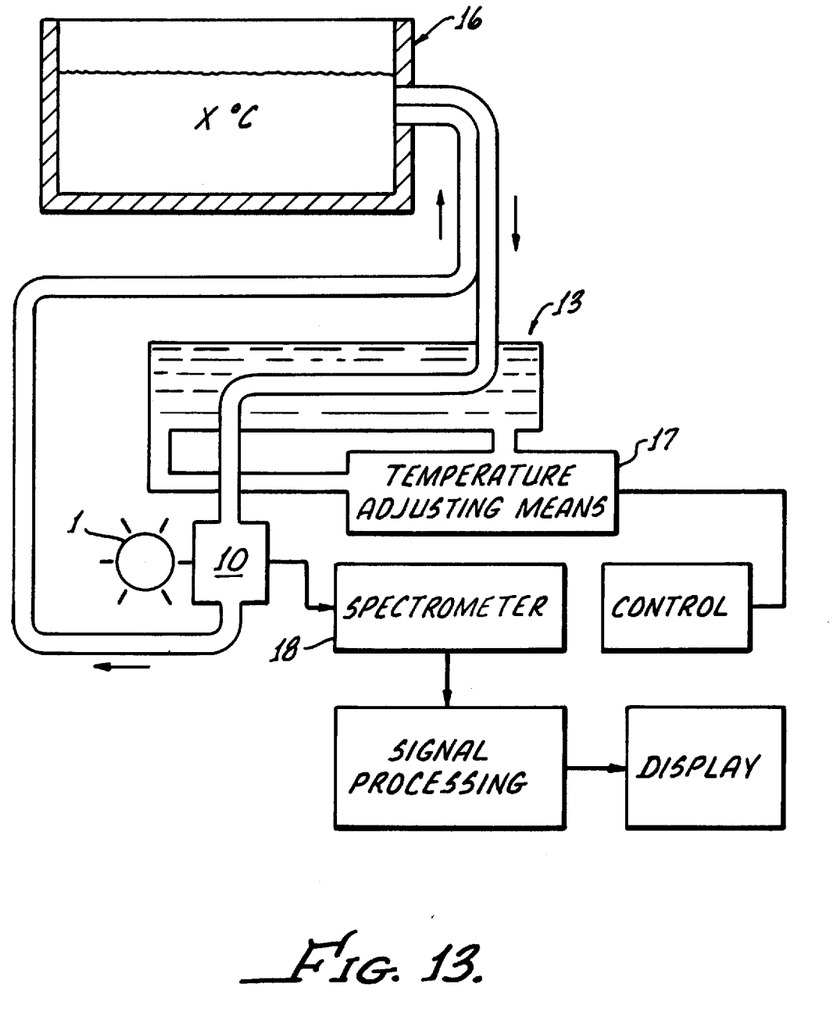
FIG. 13 is a block diagram showing an example of a conventional analytical apparatus of a multi-component aqueous solution.

In such an analytical system as shown in FIG. 13, in order to make a temperature of the multi-component aqueous solution of unknown concentrations to be measured equal to a liquid temperature of the standard solution at a calibration time, the multi-component aqueous solution (x° C.) within a chemical tank 16 has been introduced into a flow cell 10 through a thermostatic bath 13 (e.g., 25° C.), as shown in FIG. 13. In addition, reference numeral 1 designates a light source and reference numeral 18 designates a spectrometer (near-infrared spectral and detecting means).

However, in the above-described analytical system on the basis of the calibration curves, a disadvantage is present in that the accuracy of the measurement is remarkably lowered by interferences due to other components. In particular, absorbance ranges of an aqueous solution are overlapped within a near-infrared range in many cases, so that it has been difficult to eliminate influences due to other components, and it has also been considerably troublesome to draw calibration curves.

In addition, in a process using high-temperature chemicals, if chemicals cooled in the thermostatic bath 13 are returned to the chemical tank 16, a deviation from processing conditions has occurred according to such circumstances. Moreover, the thermostatic bath 13 and temperature-adjusting means 17 therefor are bulky, so that the apparatus is large so that not only is a wide installation area required but also the apparatus is complicated and expensive.

SUMMARY OF THE INVENTION

The present invention has been achieved in view of such drawbacks, and it is an object of the present invention to provide an analytical method and an analytical apparatus capable of easily, rapidly, and accurately determining concentrations of a multi-component aqueous solution, for example, as used in semiconductor processing, food processing, and the like, as well as to provide an analytical method capable of conducting temperature compensation thereof and an inexpensive analytical apparatus for the same. In order to solve the above-described problems, the present invention has the following construction.

An analytical method of the multi-component aqueous solution in which monochromatic light, which has been repeatedly scanned between desired wavelengths, is transmitted through a standard solution and a test liquid to detect absorbance thereof. Concentration values of the respective components in the multi-component aqueous solution are determined by a principal component analysis (PCA) method in the multivariate analysis on the basis of detected signals.

The invention is characterized in that near-infrared spectra of the standard solution containing k components of known concentrations are measured n times within a range of 1,500 to 1,850 nm while changing the components which change is at a compositional rate. A loading matrix of p columns by m rows and an intermediate matrix of k columns by m rows for an appointed factor number m are obtained from a response matrix of p columns by n rows consisting of p absorbance values of the respective spectra in a calibration stage FIG. 8. The p absorbance values of a near-infrared spectrum within a wavelength range of 1,500 to 1,850 nm of the test liquid containing k components including pure water of unknown concentrations are found to determine the concentrations of the k components from a group of absorbance values (vector) and the loading and intermediate matrices obtained in the calibration stage by a matrix operation in an prediction stage.

The invention is further characterized in that the number k of components is 3 to 4, the number n of spectra is 8 to 30, the number p of absorbance values is 16 to 56, and the number m of appointed factors is 4 to 7.

The invention is still further characterized in that near-infrared spectral and detecting means for selectively transmitting monochromatic light, which is repeatedly scanned between the desired wavelengths, through a standard solution or a test liquid within a flow cell to detect absorbance thereof. Computing means is provided for receiving detected signals to compute concentration values of the respective components in a multi-component aqueous solution by the analytical method set forth above.

An analytical method of the multi-component aqueous solution (in which monochromatic light, which has been repeatedly scanned between the described wavelengths, is transmitted through a standard solution and a test liquid to detect absorbance thereof and concentration values of the respective components in the multi-component aqueous solution determined by the principal component analysis (PCA) method in the multivariate analysis on the basis of detected signals) is characterized in that a solution temperature is added as one of the characteristic items to obtain an intermediate output matrix by the use of a response matrix obtained from absorbance spectra of the respective standard solutions under the desired measuring-temperature conditions in a calibration stage. An absorbance spectrum of the test liquid of unknown concentration is obtained to determine concentration values of the respective components in the test liquid from the absorbance spectrum and the intermediate output matrix obtained in the calibration stage by a matrix operation together with the solution temperature in an prediction stage.

The invention is still further characterized in that near-infrared spectral and detecting means, which is provided with a flow cell adjustable in temperature for receiving a standard solution therein and a flow cell for receiving a test liquid therein, selectively transmit monochromatic light, which has been repeatedly scanned between the desired wavelengths and through the standard solution or the test liquid within the flow cell. The computing means receives a detected signal to determine concentration values of the respective components in the test liquid together with a solution temperature by the method set forth above.

According to further aspects of the invention, in the calibration stage principal components are sampled from a response matrix consisting of n absorbance spectra (the respective spectra comprise p data). A loading matrix is in turn obtained by the principal component analysis, in which a major factor of variance (principal component) is sampled from multivariate data to simplify the data. Upon obtaining a first principal component, an absorbance matrix corresponding to the first principal component is removed from a response matrix, followed by obtaining the second to m-th principal components which are similarly removed from the response matrix, whereby the loading matrix of p columns by m rows is obtained. Simultaneously, a score matrix with the respective columns (m) and rows (n) orthogonal to those in the loading matrix is obtained FIG. 2. Subsequently, the intermediate matrix of k columns by m rows is obtained from a concentration matrix and the score matrix for the principal components 1 to k by the matrix operation.

Figure 3:
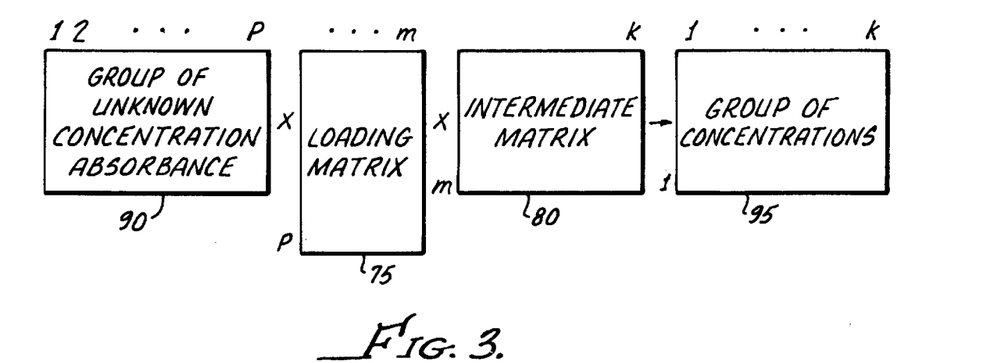
FIG. 3 is a schematic diagram showing a computing method in a prediction stage in said analytical method of a multi-component aqueous solution according to the present invention.

In the prediction stage, a group of concentrations (vector) can be obtained from the product of a group of unknown concentration absorbances (vector), the loading matrix, and the intermediate matrix FIG. 3. A difference between pure water and a hydrogen peroxide solution in absorbance may be observed in a wavelength range of 1,500 to 1,850 nm. Pure water is included in the k components of unknown concentration, so that a concentration of ammonia water and an aqueous solution of hydrogen peroxide can be detected with high accuracy in the wavelength range, respectively.

According to yet further aspects of the invention, an analytical apparatus capable of determining the concentration of multi-component aqueous solution easily, rapidly and with high accuracy is provided. New contents of a control program are set for putting the analytical method into practice in the computing means without the need to change or add other construction.

According to still further aspects of the invention, as the solution temperature is added as one of characteristic items in the calibration stage, the respective temperature-independent concentrations and the solution temperature can be simultaneously determined without requiring a temperature adjustment in the prediction stage; that is, so-called temperature compensation is possible.

According to still further aspects of the invention, a temperature setting covering the three stages of a temperature range, i.e., the upper, intermediate, and lower-limit temperature ranges, can be taken for the test liquid of a calibrating standard solution by means of a flow cell adjustable in temperature in the calibration stage. In addition, in the prediction stage, the test liquid can be analyzed easily, rapidly and with high reliability over a wide temperature range without requiring a temperature adjustment.

DETAILED DESCRIPTION OF THE PREFERRED EMBODIMENTS

The preferred embodiments of an analytical method of a multi-component aqueous solution and an analytical apparatus for the same according to the present invention will be described below in detail with reference to the drawings.

Figure 1:
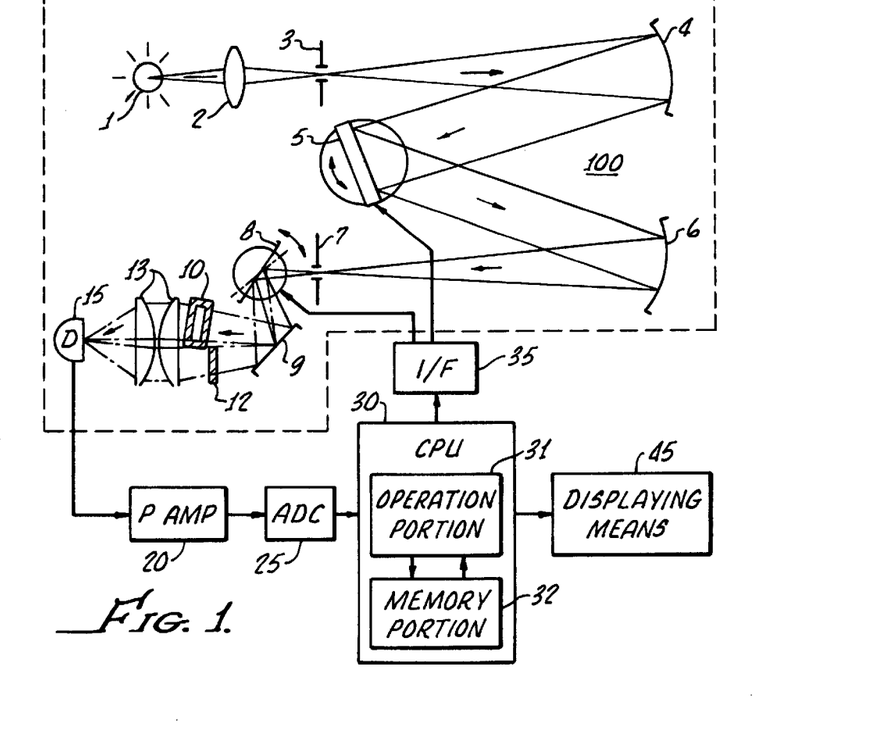
FIG. 1 is a block diagram showing a preferred embodiment of an analytical apparatus of a multi-component aqueous solution according to the present invention.

Referring to FIG. 1, a near-infrared spectral and detecting device 100 comprises a light source 1, a lens 2, an incident slit 3, a first concave spherical mirror 4, a rotatably operatable diffraction grating 5, a second concave spherical mirror 6, an emitting slit 7, a rotatably operatable flat mirror 8, a fixed flat mirror 9, a flow cell 10, a compensation plate 12, a composite lens 13, and a detector 15. Monochromatic light, which has been repeatedly scanned within an appointed or predetermined wavelength range (1,500 to 1,850 nm), is selectively transmitted through a standard solution, a test liquid, and the compensation plate 12 to detect an optical intensity thereof by means of the detector 15. A detected signal is transmitted to an operating means such as a CPU 30 through an amplifier 20 and an analog-to-digital (A/D) convertor 25 to be converted into absorbance values. Concentration values of a plurality of components of the test liquid are then obtained by a principal component analysis in a multivariate analysis, which are displayed on a display means 45. In addition, the diffraction grating 5 and the flat mirror 8 are rotatably operated by instructions from the operating means 30 through an interface 35. Moreover, the standard solution introduced into the flow cell 10 is used merely in a calibration stage, while the test liquid is introduced in an prediction stage.

Figure 2:
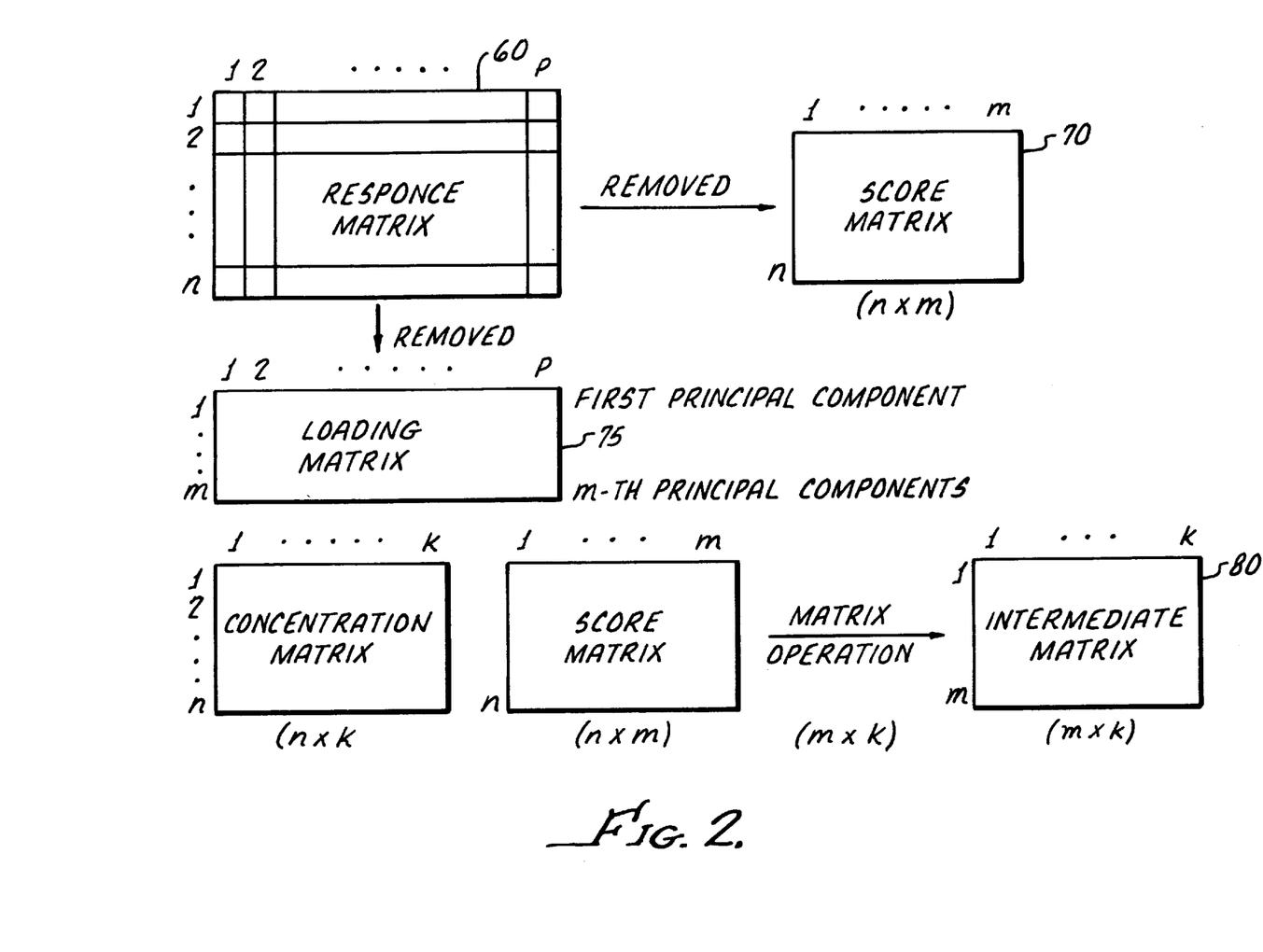
FIG. 2 is a schematic diagram showing a computing method in a calibration stage in an analytical method of a multi-component aqueous solution according to the present invention.

The analysis method will be described below. In a principal component analysis (PCA) method of the multivariate analysis, a major factor of variance (principal component) is the sampling of data from a plurality of mutually related variables to express the data by a more simple model. At first, in the calibration stage, the standard solution containing a predetermined number of k components of known concentration is introduced into the flow cell 10 to measure an absorbance thereof, whereby extracting a principal component in turn from a response matrix 60 consisting of n absorbance spectral vectors (the respective spectra consist of p data) obtains a loading matrix 175, as shown in FIG. 2.

Upon obtaining a first principal component, an absorbance matrix corresponding to the first principal component is removed from the response matrix 60, which are similarly removed from the response matrix 60, whereby a loading matrix 175 of p columns by m rows is obtained. At the same time, a score matrix 70 with its respective columns and rows orthogonal to those in the loading matrix 175 is obtained. Subsequently, an intermediate matrix 80 of k columns by m rows is obtained from a concentration matrix 65 and the score matrix 70 for the principal components 1 to k by a matrix operation set and stored in a memory portion 32 of the CPU 30.

Furthermore, the principal components are obtained as those components appearing as suitable changes in the n (8 to 30) absorbance spectral vectors (the respective vectors consist of p data) forming the response matrix 60 when concentrations of the components were changed. A number of components k is set to 3 to 4 taking reliability and the like into consideration, with pure water included as one of these components. Further, a number of absorbance values p is set to 16 to 56, and a number of appointed factors m is set to 4 to 7.

In the prediction stage, as shown in FIG. 3, a group of concentrations (vector) 95 can be obtained from the product of a group of unknown concentration (vector) 90, loading matrix 75 which is transposed from the matrix 175, and the intermediate matrix 80, read out from the memory portion 32.

In this prediction stage, a near-infrared absorbance spectrum of the test liquid (sample) flowing through the flow cell 10 can be measured to calculate the concentrations of the respective component of the test liquid whereby the concentrations are easily and rapidly displayed on the displaying means 45. In addition, influences by an absorption spectrum of a window material of the flow cell 10 and a change of light from the light source 1 in intensity can be eliminated by comparing the case where the light, which has been transmitted through the flow cell 10 with either the standard solution or the test liquid therein, is transmitted through the compensation plate 12 made of the same material and having the same thickness as the flow cell 10. In addition, in this case, in order to compare the test liquid with air, pure water is used as the first principal component to independently determine a concentration thereof separately from other components. As a result, it can be confirmed whether the total concentration of the respective components is 100% or not, whereby one is able to judge whether the measurement is correct in itself or not; thus, the analytical apparatus can maintain high reliability.

Figure 4:
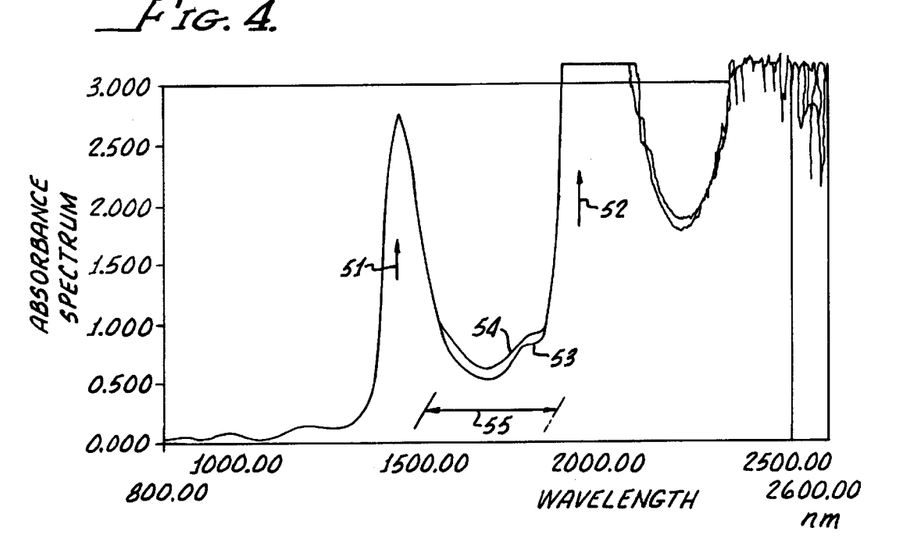
FIG. 4 is a graph showing an absorbance spectrum in a measuring wavelength range.

Moreover, a difference between pure water 53 and aqueous hydrogen peroxide solution 54 in absorbance is clearly observed in the scanning wavelength range of 1,500 to 1,850 nm, as shown by the absorbance spectra in FIG. 4. By including pure water as one of the components of unknown concentration, the concentration of ammonia water and an aqueous solution of hydrogen peroxide for use, for example, in semiconductor processing, can be accurately detected within the above-described wavelength range, respectively. Furthermore, reference numerals 51 and 52 designate absorption wavelengths of water, and reference numeral 55 designates the wavelength range of 1,500 to 1,850 nm.

The apparatus for the above-described analysis (referring to FIG. 1) can be constructed by merely setting and storing a control program for easily and rapidly conducting the above-described matrix operation in the memory portion 32 without changing the near-infrared spectral and detecting means 100 in construction or adding any new construction.

As to effects obtained by such an analytical method and analytical apparatus, at first the principal component analysis method in the multivariate analysis is used, so that interferences by other components do not come into question, and a large number of measuring wavelengths can be used, so that a signal-to-noise (S/N) ratio of the measurements can be improved, thus achieving a high analytical accuracy and a high reliability.

Further, in the matrix operation in the prediction stage, the optimum number of factors m can be appointed or predetermined, so that a highly accurate measurement value can be obtained over a wide concentration range from the same loading matrix 75 and intermediate matrix 80. Also, because of this, it is desirable that a calculation is conducted with the maximum number of factors m of the loading matrix 75 and the intermediate matrix 80 in the calibration stage equal to 7 or 8.

A near-infrared range close to the relatively weak absorbance spectra 51 and 52 of water is used, so that pure water can also be independently measured as one component of unknown concentration and that the value of the measurement can be confirmed on the basis of whether the total concentration amounts to 100% or not.

Advantageously, conditions required for the absorbance spectra according to the present invention are less severe, stringent, or absolute as compared with the conventional calibration curve methods. These conditions are itemized as follows: (1) the range, where the absorbance is unity or less, is used for an optical path length of the liquid cell used; (2) a number of wavelength points adopted may be larger than the number of components; (3) the sampling wavelengths are not always equal in interval but preferably selected so as to increase the change in absorbance; (4) wavelength points exhibiting obstructions and interferences by two or more components can also be adopted; (5) no influence is given even though k+1st unknown component, for which it is unnecessary to know the concentration not standardized in the calibration stage, is mixed; and the like.

Figure 5:
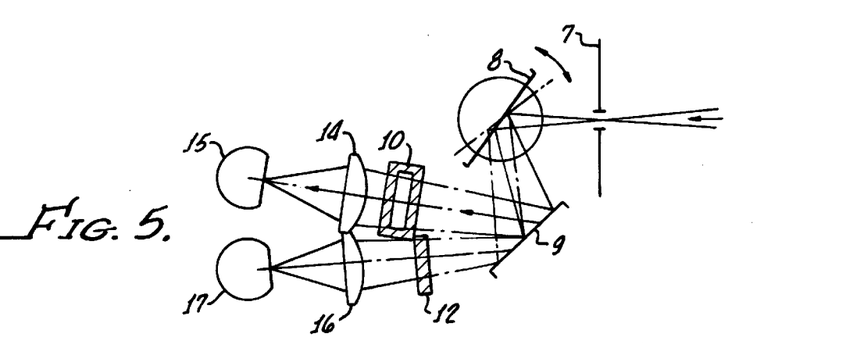
FIG. 5 is a schematic diagram showing a further embodiment of a portion of the analytical apparatus of FIG. 1.

FIG. 5 shows another preferred embodiment of the analytical apparatus according to the present invention. Two collecting lenses 14 and 16 are arranged behind a flow cell 10 and a compensation plate 12, and two detectors 15 and 17 are arranged behind the collecting lenses 14 and 16. This preferred embodiment is characterized in that monochromatic light divided by means of a rotatably operatable flat mirror 8 can be efficiently introduced to the detectors 15 and 17. In this case, the collecting lens 13 playing two parts of agreement of optical paths and collection of light, as shown in FIG. 1, is not required. It is, however, required to remove a difference between both detectors 15 and 17 in sensitivity by signal processing and the like.

Figure 6A:
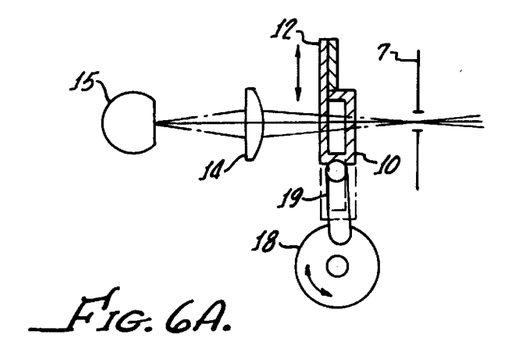
FIGS. 6(A) and 6(B) are schematic diagrams showing still further embodiments of a portion of the analytical apparatus of FIG. 1.
Figure 6B:
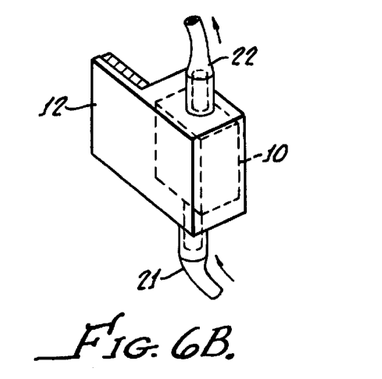

Referring to FIGS. 6(A) and 6(B), monochromatic light is alternatively transmitted through a flow cell 10 and a compensation plate 12 by reciprocal motion of a rotary disc 18 and a link 19 in place of dividing an optical path. In this case, it is necessary to introduce the standard solution and the test liquid into a flow cell 10 and discharge them from the flow cell 10 through flexible pipes 21 and 22.

Figure 7:
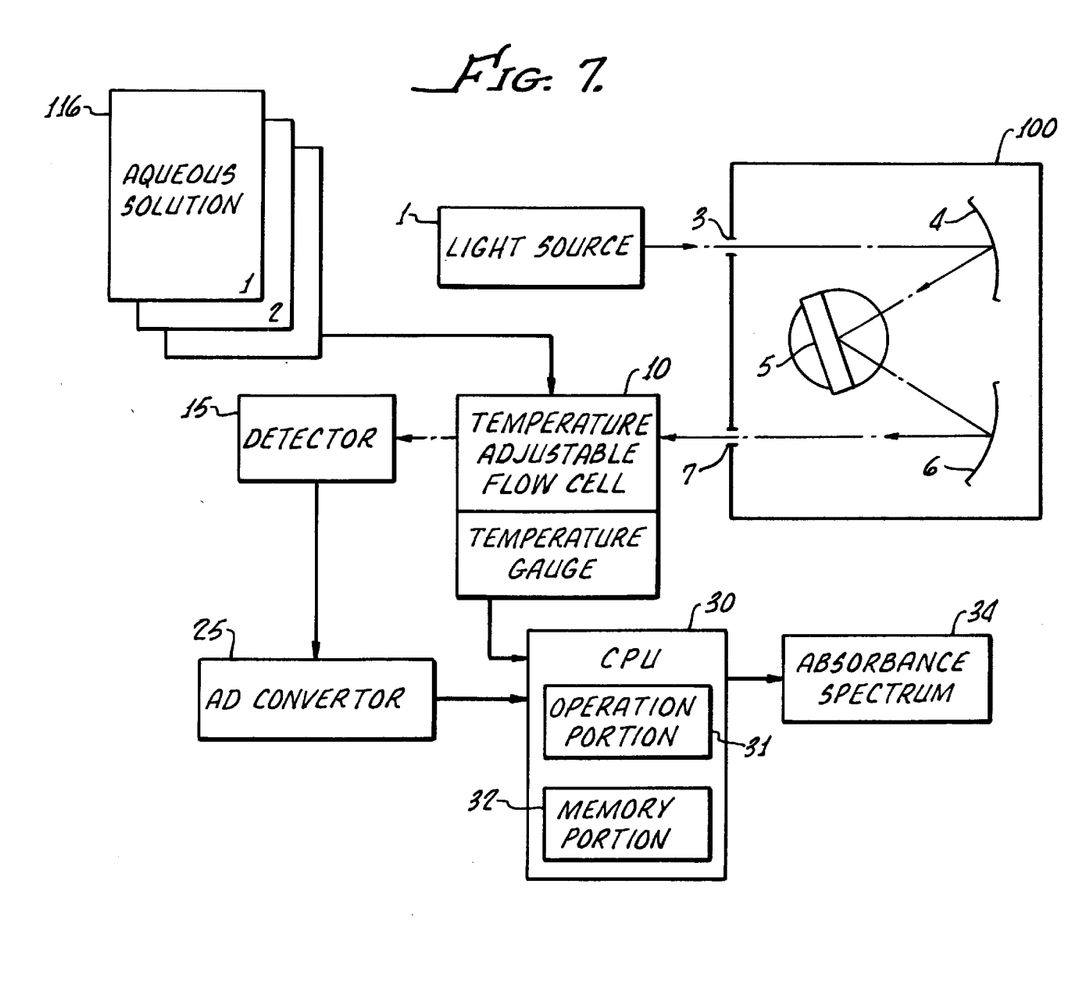
FIG. 7 is a block diagram showing principal parts used in a calibration stage in another preferred embodiment of the analytical apparatus of a multi-component aqueous solution according to the present invention.
Figure 8:
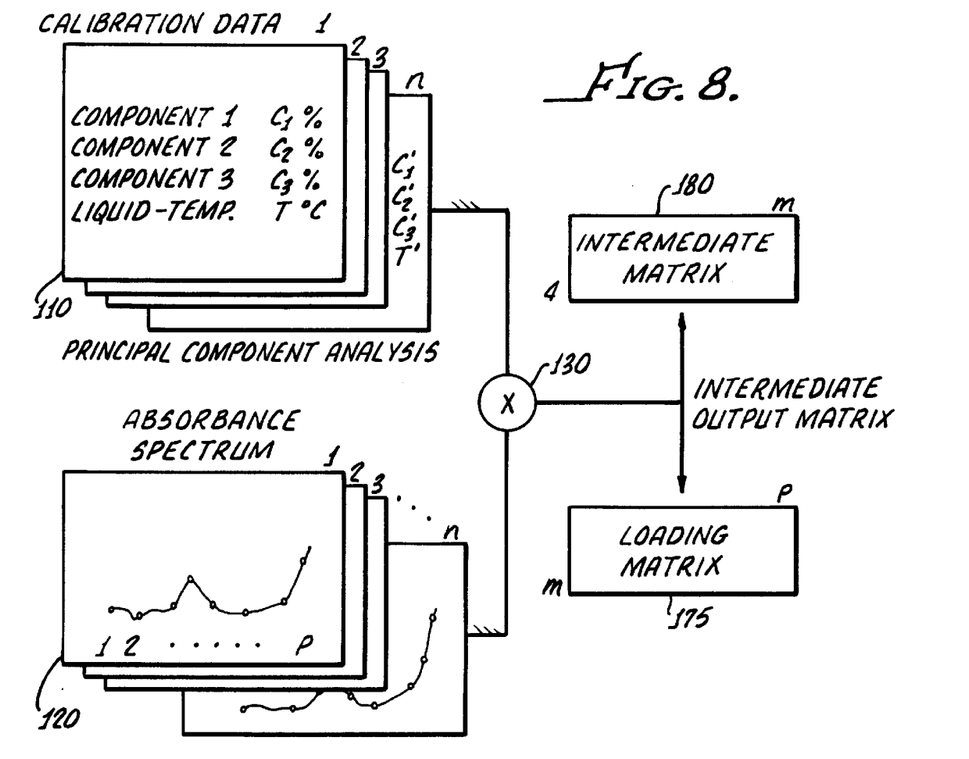
FIG. 8 is a diagram showing a computing method in the calibration stage in an analytical method according to the embodiment of FIG. 7.
Figure 9:
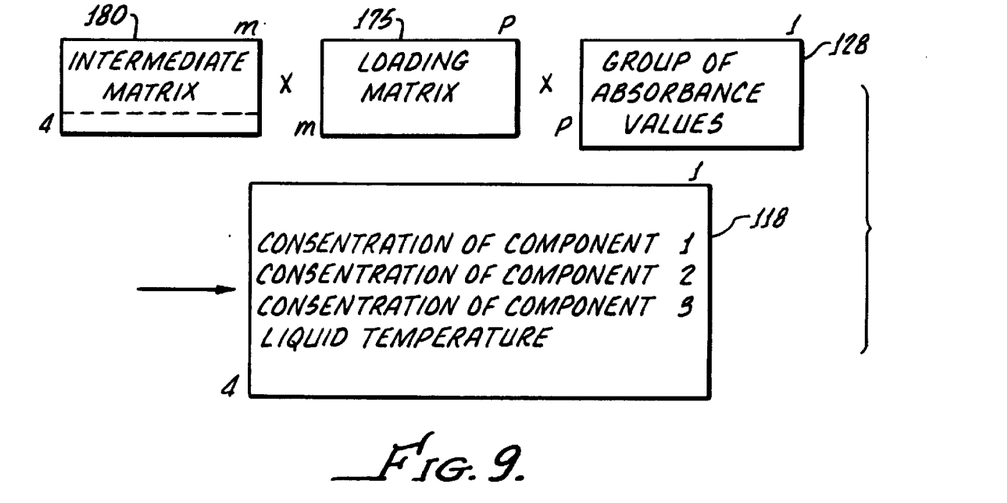
FIG. 9 is a block diagram showing a computing method in a prediction stage in an analytical method of a multi-component aqueous solution according to the preferred embodiment of FIG. 7.

FIG. 7 is a block diagram showing an analytical apparatus for conducting an analytical method capable of being compensated in temperature; FIG. 8 is a block diagram showing an operating method in the calibration stage; and FIG. 9 is a block diagram showing an operating method in the prediction stage. As shown in FIG. 8, a solution temperature (liquid temperature in ° C.) is added as one of characteristic items (calibration data) 110. Absorbance spectra (1 to n) 120 of the respective standard solutions for a first component 1, a second component 2, a third component 3, and so on are obtained under appointed measuring temperature conditions, for example, at an upper limit temperature, an intermediate temperature, and a lower-limit temperature setting. An intermediate matrix 180 and a loading matrix 175 are obtained as an intermediate output matrix from a response matrix is obtained from the absorbance spectra 120. More specifically, the respective absorbance spectra 120 corresponding to n calibration data 110 consist of p absorbance values. A number of factors m are appointed to conduct a principal component analysis 130, and the intermediate matrix 180 of m columns by 4 rows and the loading matrix 175 of p columns by m rows are calculated and stored.

Prior the above-described operation, a standard solution for use in calibration 116 (referring to FIG. 7) is poured into a liquid cell having a temperature-adjusting function (a flow cell adjustable in temperature) 10 with the optical intensity being detected by means of the detector 15. A detected signal is transmitted to an A/D converted 25 with the converted detected signal being operated on by operating means 30 which generates an absorbance spectrum 34 corresponding to appointed wavelength points. At this time, spectral data set for two to three known temperatures are measured for every standard solution.

Subsequently, in the prediction stage (referring to FIG. 9), the respective concentrations of three components and a liquid temperature 118 are simultaneously independently determined from the product of the intermediate matrix 180 and the loading matrix 175 obtained in the calibration stage, and a group of absorbance values (vector) 128 for every appointed wavelength of the test liquid of unknown concentration is determined. In short, the temperature characteristics can be compensated without adjusting a temperature of the test liquid.

Figure 10:
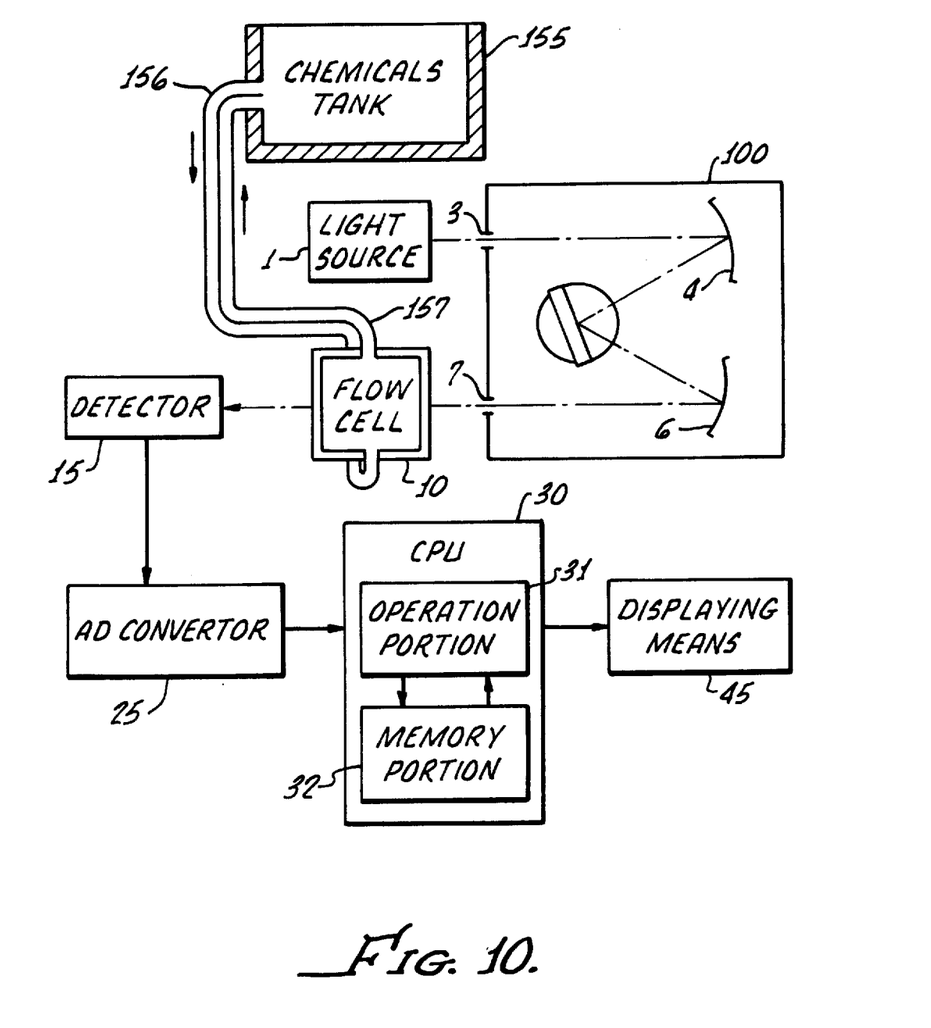
FIG. 10 is a schematic block diagram showing principal parts used in the prediction stage in the preferred embodiment of FIG. 7.

A measuring system in the above-described prediction stage is shown, for example, in FIG. 10. A chemical tank 155 stores the test liquid (chemicals) of unknown concentration. An extracting pipe 156 extends from the chemical tank 155 to a flow cell 10. A circulating pipe 157 extends from the flow cell 10 to the chemical tank 155. The test liquid is introduced into the flow cell 10 without adjusting temperature to detect an absorbance thereof, thereby obtaining the group of absorbance values 128 (referring to FIG. 9), followed by reading out the intermediate matrix 180 and the loading matrix 175 stored in the calibration stage to easily and rapidly determine the concentration and the temperature by a matrix operation. In addition, as shown in FIGS. 7 and 10, an apparatus used in the prediction stage may be different from that used in the calibration stage. This point is similar also in the preferred embodiment shown in FIG. 1. In the calibration stage using the standard solution, a standard machine for obtaining intermediate output matrices 75 and 80 commonly stored in the respective apparatus is used, which machine may be different from a concentration-analyzing apparatus used in the prediction stage. It goes without saying, however, that a reproducibility of wavelengths in both machines is required; in short, it is required that wavelengths are set within an appointed (narrow) range.

Such an analytical method and analytical apparatus lead to the following effects. At first, it is not required to adjust the test liquid in temperature, so that a thermostatic bath is not required; as such the apparatus is inexpensive and can cope with (i.e., compensate) a wide temperature range (about ° 20 to 90° C.) of chemicals in semiconductor processing and the like. Subsequently, the liquid temperature can be measured at the same time as the concentrations of the respective components. In addition, a reliability of concentration monitors can be checked by separately providing a liquid temperature sensor for the test liquid. Moreover, the method according to the above-described preferred embodiment can be incorporated with this method. Furthermore, it is not required that the liquid temperature of the standard solution be held constant in the calibration stage, but it is generally required that it is moderately dispersed within a range meeting the temperature conditions of the test liquid. However, the optimum set value will be able to be found in dependence upon environmental conditions of an individual test liquid and the like.

In an exemplary embodiment of the invention, a circulating method of the test liquid is shown in FIG. 10. It is thought that the test liquid is not returned to the chemical tank 155 according to processes but subjected to a batch treatment to be dumped after every measurement. In addition, it is known that a short wavelength-cutting filter is provided in an optical path of the spectrometer 100 (shown in FIG. 1) in order to remove influences by visible higher-order (2nd to 4th order) light having short wavelengths. However, the adjustment can be more easily confirmed in the case where a beam can be visually observed, so that it is preferable that the short wavelength-cutting filter (not shown) is arranged immediately before the detector 15.

Although the absorbance spectra of a hydrogen peroxide solution and pure water were shown in FIG. 4 as the absorbance spectra of the representative aqueous solutions, it goes without saying that a similar absorbance spectrum is obtained also for ammonia water. Furthermore, although an order of the matrix product in the prediction stage shown in FIG. 3 is different from that shown in FIG. 9 a difference consists in that group of absorbance values for unknown concentrations is a horizontal vector 90 or a vertical vector 128; thus, quite similar results are obtained.

Figure 11:
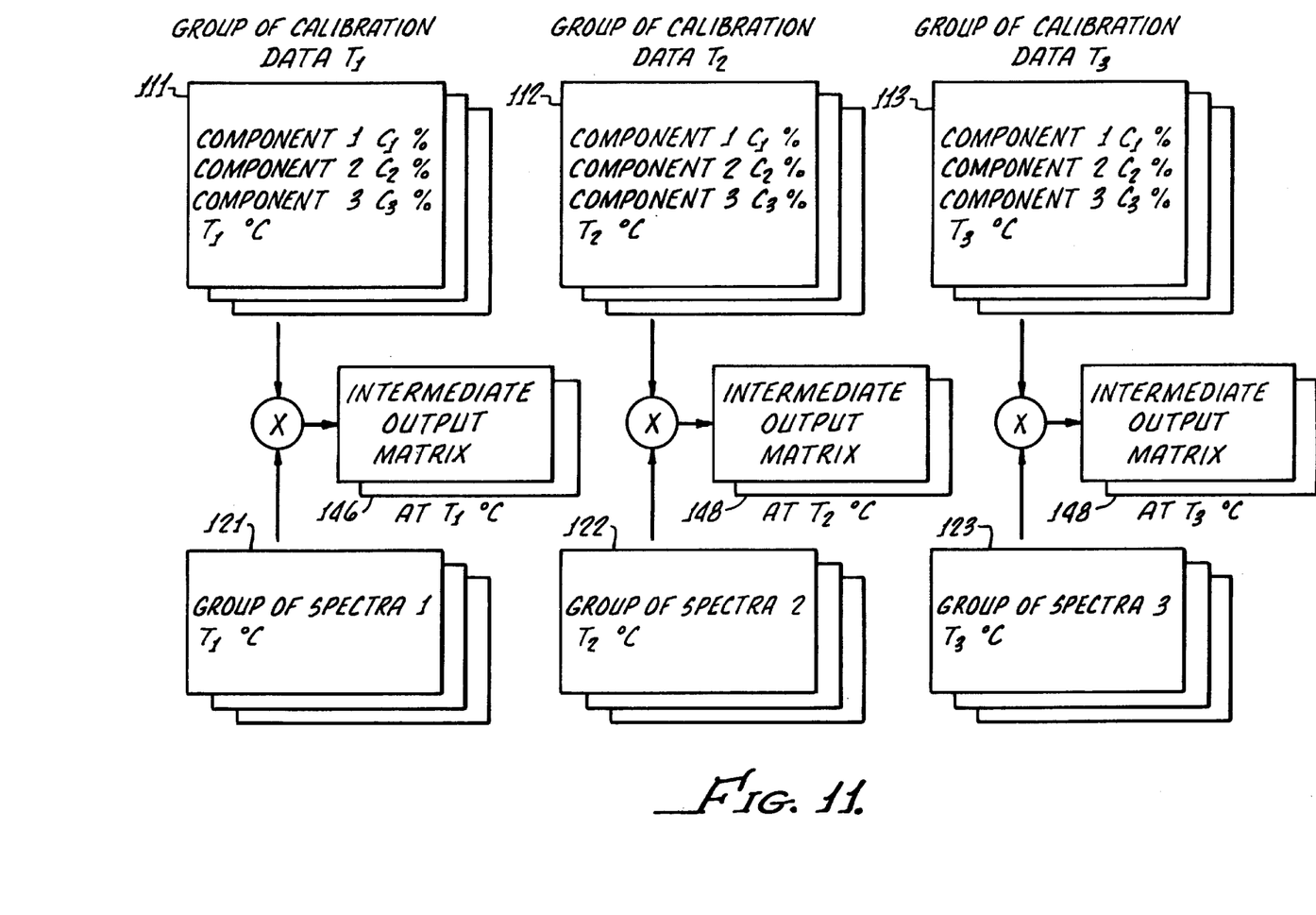
FIG. 11 is a block diagram showing exemplary embodiments of the analytical method of a multi-component aqueous solution according to the present invention.

Additionally, as to a method of compensating the temperature characteristics of the multi-component aqueous solution using the near-infrared spectral and detecting means and the principal component analysis method, the calibration is conducted for every one of a plurality of temperatures within the desired temperature range as shown in FIG. 11. For example, intermediate output matrices 146, 147, 148 for the respective temperatures $T_1$, $T_2$, $T_3$ are previously obtained from groups of calibration data 111, 112, 113 and groups of spectra 121, 122, 123 corresponding to the respective temperatures $T_1$, $T_2$, $T_3$. In a measurement of the test liquid of unknown concentration, the solution temperature is firstly measured to select a set of intermediate output matrices corresponding to the temperature, which is followed by obtaining a component concentration by the use of the intermediate matrix and the loading matrix. However, in this case, it is required to strictly control the temperature for every group of temperatures in the calibration stage.

As described above, according to the present invention, pure water is included as one of the components of unknown concentration of the test liquid of which concentration is to be measured, so that a difference between pure water and ammonia water, hydrogen peroxide or the like in absorbance is clearly observed in the wavelength range of 1,500 to 1,850 nm. Consequently, the respective concentrations of ammonia water, the aqueous solution of hydrogen peroxide and the like often used in, for example, semiconductor processing and the like, can be obtained easily, rapidly and with high accuracy. In addition, this has an advantage in that the measured value can be confirmed by judging whether the total concentration value including the concentration of pure water measured independently as one component amounts to 100% or not. Furthermore, the effects due to the use of the principal component analysis in the multivariate analysis are increased. That is, the influences by other components do not come into question at the measuring wavelengths. Accordingly, a large number of measuring wavelengths can be used,, the signal-to-noise ration is improved, and high reliability is achieved. In addition, in the matrix operation in the prediction stage, the optimum number of factors m can be appointed, and thus highly accurate results of measurement can be obtained over the wide concentration range by the use of the same loading matrix and intermediate matrix, prepared with the maximum factor number at the calibration stage.

According to the further aspects of the invention, the analytical apparatus is capable of determining the concentration of multi-component aqueous solution easily, rapidly, and with high accuracy by merely setting new contents of a control program for putting the inventive analytical method into practice in the computing means which is inexpensive, without changing the construction thereof or adding new construction.

According to still further aspects of the invention as the solution temperature is added as one of characteristic items in the calibration stage, the respective concentrations and the solution temperature (characteristics) can be simultaneously determined without requiring a temperature adjustment in the prediction stage; that is, so-called temperature compensation in the concentration analysis becomes possible so that the compensation can be conducted for chemicals having temperatures over the wide temperature range (about 20° to 90° C.) in semiconductor processing and the like. In addition, it is also possible to check the concentration monitor with reliability from the stability of the difference between both temperatures by separately providing a liquid temperature sensor for the test liquid.

According to yet further aspects of the invention, the appropriate temperature setting of the calibrating standard solution becomes possible by means of the flow cell being adjustable in temperature in the calibration stage. In addition, in the prediction stage, it is not required to adjust the test liquid in temperature, so that a thermostatic bath is not required, resulting in more compact apparatus. Consequently, the analytical apparatus capable of analyzing the test liquid easily, rapidly, and with high reliability over the wide temperature-range can be inexpensively provided.

What is claimed is:

1. A method for analyzing a multi-component aqueous solution, comprising the steps of:

providing a test liquid containing k components of unknown concentrations;

providing a standard solution containing k components of known concentrations and at a first plurality of known temperatures;

transmitting monochromatic light which has been repeatedly scanned in a wavelength range of 1,500 nm to 1,850 nm through said test liquid and said standard solution;

measuring n near-infared spectra of said standard solution within said wavelength range at said first plurality of known temperatures;

detecting p absorbance values of n spectra of said standard solution and p absorbance values of said test solution at a second plurality of temperatures;

generating response matrix of n columns by p rows comprising said absorbance values of respective spectra of said standard solution at first plurality of known temperatures and said p absorbance values of a near-infrared spectrum within said wavelength range of said test liquid;

obtaining a loading matrix of p columns by m rows and an intermediate matrix of m columns by k rows for an appointed factor number m from said response matrix; and determining concentrations of said k components of said test solution from a group of said absorbance values for said test solution and said loading and intermediate matrices by a matrix operation.

2. The method of claim 1 further comprising the following step prior to said transmitting step:

maintaining said standard solution and said test solution within a predetermined temperature range.

3. The method of claim 1 wherein:

said k components of said standard solution is in an approximate range of three to four;

said n times of measuring of near-infrared spectra is in an approximate range of eight to 30;

said p absorbance values of said standard and said test solution is in an approximate range of 16 to 56; and said appointed factors number m is in an approximate range of four to seven.

4. A method for determining concentrations of a solution, comprising the steps of:

obtaining absorbance values of a standard solution containing a plurality of known components of known concentrations and at a first plurality of known temperatures within a predetermined wavelength range;

obtaining absorbance values of a test solution containing a plurality of said known components of unknown concentrations at a second plurality of temperatures within said predetermined wavelength range;

generating response matrices comprising said absorbance values of said standard solution at said first plurality of known temperatures;

generating a loading matrix comprising principal components extracted from said response matrix;

generating a score matrix orthogonal to said loading matrix from said response matrix;

generating a concentration matrix comprising said components;

generating an intermediate matrix by performing a matrix operation on said concentration matrix and said score matrix;

generating a concentration absorbance matrix from said absorbance values of said test solution; and generating a concentration vector of concentration values of said plurality of components of said test solution by performing matrix operations on said concentration absorbance matrix, said loading matrix, and said intermediate matrix.

5. The method of claim 4 wherein said step of obtaining absorbance values of a test solution comprises the step of:

obtaining absorbance values of a test solution containing a plurality of components including water of unknown concentrations.

6. The method of claim 4 wherein said predetermined wavelength range is approximately 1,500 nm to 1,850 nm.

7. The method of claim 4 wherein said two steps of obtaining absorbance values comprise the steps of:

obtaining a predetermined number of absorbance values of a standard solution containing a plurality of components of known concentrations within a predetermined wavelength range; and obtaining a predetermined number of absorbance values of a test solution containing a plurality of components of unknown concentrations within said predetermined wavelength range.

8. A method for analyzing a multi-component aqueous solution, comprising the steps of:

providing a test liquid containing k components of unknown concentrations;

providing a standard solution containing k components of known concentrations and at a first plurality of known temperatures, said standard solution including pure water and having a temperature;

transmitting monochromatic light which has been repeatedly scanned in a predetermined wavelength range through said test liquid and said standard solution;

measuring n spectra of said standard solution simultaneously at said first plurality of known temperatures and changing ratio between said components within said predetermined wavelength range;

detecting p absorbance values of n spectra of said standard solution and p absorbance values of said test solution at a second plurality of temperatures;

generating response matrices of n columns by p rows comprising said absorbance values of respective spectra of said standard solution at said first plurality of known temperatures, including that of said pure water, and said p absorbance values of a near-infrared spectrum within said wavelength range of said test liquid;

obtaining a loading matrix of p columns by m rows and an intermediate matrix of m columns by k rows for an appointed factor number m from said response matrix; and determining concentrations of said k components of said test solution from a group of said absorbance values for said test solution and said loading and intermediate matrices by a matrix operation.

9. The method of claim 8 wherein said predetermined wavelength range is approximately 1,500 nm to 1,850 nm.

10. The method of claim 8 wherein said spectra is near-infrared spectra.

11. A method for analyzing a multi-component aqueous solution, comprising the step of:

providing a test liquid containing k components of unknown concentrations into a liquid cell;

providing a standard solution containing k components of known concentrations at first plurality of known temperatures;

transmitting monochromatic light which has been repeatedly scanned in a predetermined wavelength range through said test liquid and said standard solution;

measuring n spectra and said temperature of said standard solution at said first plurality of known temperatures and changing ratios between components within said wavelength range;

detecting p absorbance values of n spectra of said standard solution at a second plurality of temperature and p absorbance values of said test solution;

generating response matrices of n columns by p rows comprising said absorbance values of respective spectra of said standard solution at said first plurality of known temperatures and said p absorbance values of a near-infrared spectrum within said wavelength range of said test liquid;

obtaining a loading matrix of p columns by m rows and an intermediate matrix of m columns by k rows for an appointed factor number m from said response matrix; and determining concentrations of said k components of said test solution from a group of said absorbance values for said test solution and said loading and intermediate matrices by a matrix operation.

12. The method of claim 11 wherein said standard solution includes pure water.

13. The method of claim 11 further comprising the step of controlling a temperature of said liquid cell.

14. The method of claim 11 wherein said predetermined wavelength range is approximately 1,500 nm to 1,850 nm.

15. The method of claim 11 wherein said spectra is near-infrared spectra.

* * * * *

UNITED STATES PATENT AND TRADEMARK OFFICE
CERTIFICATE OF CORRECTION

PATENT NO. : 5,886,347
DATED : March 23, 1999
INVENTOR(S) : Masaru Inoue; Juichiro Ukon; Issei Yokoyama; Takashi Hagiwara It is certified that error appears in the above-indentified patent and that said Letters Patent is hereby corrected as shown below:

Column 10, line 4, delete the word "matrix" and insert the word --matrices--.

Column 10, line 6, between the terms "at" and "first" insert --said--.

Column 10, line 31, between the terms "of" and "a" insert --components of--.

Column 10, line 48, between the terms "said" and "components" insert --principal--.

Column 11, line 26, delete the word "ratio" and insert --ratios--.

Signed and Sealed this

Thirty-first Day of August, 1999

Q. TODD DICKINSON

*Attest:*

*Attesting Officer*     *Acting Commissioner of Patents and Trademarks*